United States Patent
Mac Dermott et al.

(10) Patent No.: US 9,895,295 B2
(45) Date of Patent: *Feb. 20, 2018

(54) SOLID COSMETIC COMPOSITION IN COMPACT POWDER FORM

(75) Inventors: Padraig Mac Dermott, Meudon (FR); Gwenola Le Gars, Paris (FR); Xavier Blin, Paris (FR)

(73) Assignee: L'OREAL, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/241,704

(22) PCT Filed: Jul. 27, 2012

(86) PCT No.: PCT/EP2012/064780
§ 371 (c)(1),
(2), (4) Date: Feb. 27, 2014

(87) PCT Pub. No.: WO2013/041274
PCT Pub. Date: Mar. 28, 2013

(65) Prior Publication Data
US 2014/0227216 A1    Aug. 14, 2014

Related U.S. Application Data

(60) Provisional application No. 61/595,173, filed on Feb. 6, 2012.

(30) Foreign Application Priority Data

Sep. 21, 2011  (FR) ...................... 11 58378

(51) Int. Cl.
| | | |
|---|---|---|
| *A61K 8/02* | (2006.01) | |
| *A61K 8/19* | (2006.01) | |
| *A61K 8/891* | (2006.01) | |
| *A61Q 1/12* | (2006.01) | |
| *A61K 8/36* | (2006.01) | |
| *A61K 8/37* | (2006.01) | |
| *A61K 8/96* | (2006.01) | |
| *A61Q 1/02* | (2006.01) | |
| *A61K 8/92* | (2006.01) | |
| *A61K 8/26* | (2006.01) | |
| *A61Q 1/08* | (2006.01) | |

(52) U.S. Cl.
CPC ............... *A61K 8/022* (2013.01); *A61K 8/02* (2013.01); *A61K 8/0279* (2013.01); *A61K 8/19* (2013.01); *A61K 8/26* (2013.01); *A61K 8/361* (2013.01); *A61K 8/37* (2013.01); *A61K 8/375* (2013.01); *A61K 8/891* (2013.01); *A61K 8/92* (2013.01); *A61K 8/965* (2013.01); *A61Q 1/02* (2013.01); *A61Q 1/12* (2013.01); *A61Q 1/08* (2013.01)

(58) Field of Classification Search
CPC ... A61Q 1/12; A61K 8/19; A61K 8/92; A61K 8/022
USPC ......................................................... 424/401
See application file for complete search history.

(56) References Cited

U.S. PATENT DOCUMENTS

2010/0196484 A1* 8/2010 Aubrun .................. A61K 8/19
424/489

FOREIGN PATENT DOCUMENTS

| EP | 2186544 A1 * | 5/2010 | ............... A61K 8/19 |
| WO | WO 2010109545 A1 * | 9/2010 | |

OTHER PUBLICATIONS

ImerCare technology information, World Minerals, Feb. 2011.*
International Search Report dated Dec. 13, 2012 in PCT/EP12/064780 Filed Jul. 27, 2012.

* cited by examiner

*Primary Examiner* — Gina C Justice
(74) *Attorney, Agent, or Firm* — Oblon, McClelland, Maier & Neustadt, L.L.P.

(57) ABSTRACT

The present invention relates to a solid cosmetic composition in the form of a powder, which is preferably compacted, comprising at least: —a pulverulent phase in an amount of greater than or equal to 35% by weight relative to the total weight of the composition, comprising at least one perlite in the form of particles in a content of greater than or equal to 20% by weight relative to the total weight of the composition, —a liquid fatty phase, and in which the perlite particles and the liquid fatty phase are present in the composition in a respective total content such that the weight ratio of the perlite particles to the liquid fatty phase ranges from 2 to 25. The present invention also relates to a process for coating the face, and in particular the cheeks, the chin, the temples, the forehead and the nose, with the said cosmetic composition.

17 Claims, No Drawings

SOLID COSMETIC COMPOSITION IN COMPACT POWDER FORM

This application is a National Stage of PCT/EP12/064780 filed Jul. 27, 2012 and claims the benefit of U.S. Ser. No. 61/595,173 filed Feb. 6, 2012 and FR 1158378 filed Sep. 21, 2011.

The present invention targets the field of care and/or makeup solid cosmetic compositions, and more specifically compositions in loose or compact powder form. The invention also relates to a process for coating the skin, and in particular the face, with the said cosmetic composition.

The cosmetic compositions in accordance with the invention, especially makeup compositions such as foundation powders, are in a powder form and mainly concern compositions conventionally termed "compact powders" or "loose powders".

In general, these compositions in powder form combine a pulverulent phase that is generally predominant with a binder phase usually featured by a liquid fatty phase. The pulverulent phase is formed essentially of fillers optionally combined with colouring agents, the amount of these colouring agents being modified to afford the desired makeup effect.

These powders are generally applied to the skin using an applicator, for instance a sponge, a puff or a brush.

The function of the abovementioned powders is mainly to give colour, mattness and even, for those more particularly intended for facial skin, to improve the wear properties of a foundation powder or, if used alone, to give coverage. These galenical forms are particularly appreciated by users with regard to their lightness, softness, tack-free aspect or non-greasy feel.

Specifically, besides an aesthetic makeup effect, the user generally expects from the use of such products firstly wear comfort and application comfort and secondly good staying power over time. The wear comfort and application comfort properties are especially reflected by qualities such as softness, fluidity, glidance and meltability on the skin, and by a very fine and creamy texture. Now, for the reasons mentioned hereinbelow, reconciliation of these two aspects, wear comfort and application comfort, and staying power over time, in the same composition, is not entirely optimized.

Specifically, the fluidity and/or softness aspect on application is generally associated with the nature and amount of binder retained. A composition should normally contain a sufficient amount of binder to ensure that it has a homogeneous appearance, to give it good spreadability on application, to prevent impairment of the makeup over time, and in addition, in the particular case of compact powders, to ensure their good erodability, a cohesive aspect, and to prevent their fragmentation liable to be caused especially by impacts.

Furthermore, this amount of binder may impair the availability of the fillers, resulting in a decrease in the capacity for absorbing water, sweat and/or sebum, resulting in a shiny, glossy skin effect.

Moreover, to obtain a composition in compact solid form, pressed or compacted makeup powders formed by a mixture of powders with a fatty binder are formed by pressing (at about 10 bar) or compacting (at about 100 bar). One drawback associated with such compacted powders is that they may be brittle, i.e. have poor impact strength.

To overcome this, one solution then consists in increasing the amount of fatty binder, but to the detriment of the availability of the fillers for absorbing water, sweat and/or sebum and consequently the efficacy of these fillers.

Furthermore, such a composition will have a tendency to become waxy, i.e. to harden during use to the point that it cannot be taken up. Such compositions are also extremely difficult to compact, as a result of which pressing is quite often performed under lower pressing conditions. However, once pressed, these compositions remain fragile and have a tendency to disintegrate or even to break, for example when the product is dropped.

Consequently, there remains at the present time a need for solid cosmetic compositions in loose or compact powder form which are intended especially for making up the skin, and which are entirely satisfactory in terms of the properties of comfort on application and during wear, staying power over time, coverage and remanence of the matt effect over time. As regards compact powders, there is a need to provide compact powder compositions having fillers that are available to ensure good retention of fat-based or water-based bodily fluids and that are preferably resistant to impacts.

One aim of the present invention is thus to obtain makeup compositions in the form of powders, for example loose or compact powders, preferably compacted powders, which show good homogenization and, where appropriate, good cohesion.

An aim of the present invention is also to obtain makeup compositions in the form of powders, for example compact powders, which are easy to compact, and preferably without any excess of liquid fatty phase.

An aim of the present invention is also to obtain makeup compositions in compact powder form that erode easily.

An aim of the present invention is also to obtain makeup compositions in the form of powders, for example loose or compact powders, which have improved filler availability qualities, ensuring good efficacy of these fillers from the point of view of absorption of water, sweat and/or sebum.

One aim of the present invention is also to obtain makeup compositions in the form of loose or compact powders, which show good adhesion to keratin materials to be made up, in particular the cheeks, especially good staying power over time (such as eight hours), for example with respect to water or rubbing.

An aim of the present invention is also to obtain makeup compositions in the form of powders, for example loose or compact powders, which show good remanence of the matt effect over time (for example eight hours).

An aim of the present invention is also to obtain makeup compositions in the form of powders, for example loose or compact powders, which give a natural, "transparent" makeup effect, thus making it possible to vary the colour effects at will depending on the ethnic nature of the skin surface to be made up.

An aim of the present invention is also to make a makeup composition in the form of powders, for example loose or compact powders, which is comfortable on application, i.e. which does not pull on the made-up skin surface.

An aim of the present invention is also to obtain makeup compositions in the form of powders, for example loose or compact powders, which offer satisfactory cosmetic qualities, thus allowing a makeup result that is uniform, and/or without any overthickness or any material effect.

An aim of the present invention is also to obtain makeup compositions in the form of powders, for example loose or compact powders, which do not become waxy over time, thus conserving their uptake and erosion qualities.

An aim of the present invention is also to obtain makeup compositions in the form of powders, for example loose or compact powders, which do not crack over time.

An aim of the present invention is also to obtain impact-resistant makeup compositions in compact powder form.

To do this, according to a first aspect, one subject of the present invention is a solid makeup and/or care cosmetic composition in the form of a powder comprising at least:
- a pulverulent phase in an amount of greater than or equal to 35% by weight relative to the total weight of the composition, comprising at least one perlite in the form of particles in a content of greater than or equal to 20% by weight relative to the total weight of the composition,
- a liquid fatty phase, and in which the perlite particles and the liquid fatty phase are present in the composition in a respective total content such that the weight ratio of the perlite particles to the liquid fatty phase ranges from 2 to 25, more preferentially from 4 to 20 and even more preferentially from 5 to 10.

A composition according to the invention is preferably of the leave-in type.

Such a composition is preferably obtained via a compacting manufacturing process.

Such a composition may thus make it possible to formulate foundation powders comprising a high content of lamellar fillers.

The texture of such a composition allows the application to the skin of a smooth, uniform film, which has good staying power properties over time and good remanence of the matt effect over time.

Finally, this composition, when compact, remains particularly resistant to impacts. Furthermore, it is easy to erode.

For the purposes of the present invention, the following definitions apply:

"solid" means the state of the composition at room temperature (25° C.) and at atmospheric pressure (760 mmHg), i.e. a composition of high consistency, which conserves its form during storage. As opposed to "fluid" compositions, it does not flow under its own weight. It is advantageously characterized by a hardness as defined below.

"compact powder" means a mass of product whose cohesion is at least partly provided by compacting during the manufacture. In particular, by taking a measurement using a TA.XT.plus Texture Analyser texturometer sold by the company Stable Micro Systems, the compact powder according to the invention may advantageously have a pressure resistance of between 0.1 and 1 kg and especially between 0.2 and 0.8 kg, relative to the surface area of the spindle used (in the present case 7.07 mm$^2$). The measurement of this resistance is performed by moving an SMS P/3 flat-ended cylindrical cylinder in contact with the powder over a distance of 2 mm at a speed of 0.5 mm/second; more generally, this powder is obtained by compacting. The term "compact powder" should be understood more precisely to mean that these powders have a shore A hardness, measured using a Zwick durometer, which ranges, according to the intensity of the shades under consideration, from 12 to 30° Shore A.

the term "loose powder" means a mass of product that is capable of collapsing under its own weight; such a mass being formed by particles that are predominantly isolated and mobile relative to each other, the term "leave-in" means a composition that is not intended to be washed out or removed immediately after application.

Preferably, the composition according to the invention comprises less than 3% by weight and preferably less than 2% by weight of water relative to the total weight, or even is free of water.

The composition according to the invention advantageously comprises a solids content of greater than or equal to 95%, better still 98%, or even equal to 100%.

For the purposes of the present invention, the "solids content" denotes the content of non-volatile matter.

The solids content (abbreviated as SC) of a composition according to the invention is measured using a "Halogen Moisture Analyzer HR 73" commercial halogen desiccator from Mettler Toledo. The measurement is performed on the basis of the weight loss of a sample dried by halogen heating, and thus represents the percentage of residual matter once the water and the volatile matter have evaporated off.

This technique is fully described in the machine documentation supplied by Mettler Toledo.

The measuring protocol is as follows:

Approximately 2 g of the composition, referred to hereinbelow as the sample, are spread out on a metal crucible, which is placed in the halogen desiccator mentioned above. The sample is then subjected to a temperature of 105° C. until a constant weight is obtained. The wet mass of the sample, corresponding to its initial mass, and the dry mass of the sample, corresponding to its mass after halogen heating, are measured using a precision balance.

The experimental error associated with the measurement is of the order of plus or minus 2%.

The solids content is calculated in the following manner:

$$\text{Solids content(expressed as weight percentage)}=100\times(\text{dry mass/wet mass}).$$

The composition may comprise a pulverulent phase greater than or equal to 50% by weight, better still 60% by weight, better still 80% by weight, preferentially 90% by weight and more preferentially 95% by weight relative to the total weight of the composition.

The pulverulent phase advantageously comprises at least one colouring agent chosen from pigments. This pulverulent phase preferably comprises more generally at least one colouring agent chosen from nacres, pigments and reflective particles, and mixtures thereof.

The said composition advantageously has a content of colouring agent, and in particular of pigment(s), of greater than or equal to 0.01% by weight relative to the total weight of the composition.

The said composition may comprise a content of pigments of ranging from 0.1% to 40% by weight and better still from 1% to 30% by weight relative to the total weight of the composition.

The liquid fatty phase may be present in a content of less than or equal to 15% by weight relative to the total weight of the composition, preferably less than or equal to 10% by weight relative to the total weight of the composition, for example between 2% and 8% by weight relative to the total weight of the composition. The liquid fatty phase may comprise at least one non-volatile oil chosen from non-volatile hydrocarbon-based and silicone oils, and mixtures thereof.

The said composition may comprise at least one additional filler. The additional filler(s) may comprise at least one mineral filler. The additional filler(s) may comprise at least one organic filler. The additional filler(s) may comprise at least one lamellar filler. The additional filler(s) may be chosen predominantly, or even exclusively, from one or more lamellar fillers. The additional filler(s) may be present in a content of greater than or equal to 20% by weight relative to the total weight of the composition. The additional filler(s) may be chosen from talc, mica and sericite, and mixtures thereof.

The composition preferably comprises at least 75% by weight, better still at least 85% by weight, even better still at least 95% by weight and even more preferentially 100% by weight of mineral fillers relative to the total weight of fillers (it being understood that the mineral fillers correspond to the perlite particles and, when present, to the additional fillers present in the said composition).

The composition preferably comprises at least 75% by weight, better still at least 85% by weight, even better still at least 95% by weight and even more preferentially 100% by weight of lamellar fillers relative to the total weight of fillers (it being understood that the lamellar fillers correspond to the perlite particles and, when present, to the additional fillers present in the said composition).

The perlite particles and the additional filler(s) may be present in the composition in a respective total content such that the weight ratio of the perlite particles to the additional filler(s) may range from 0.2 to 3, preferentially from 0.25 to 1 and better still from 0.3 to 0.8.

The perlite particles and the pulverulent phase may be present in the composition in a respective total content such that the weight ratio of the perlite particles to the pulverulent phase ranges from 0.2 to 1, better still from 0.22 to 0.95, even better still from 0.25 to 0.9, preferably from 0.30 to 0.75 and more preferentially from 0.4 to 0.6.

The pulverulent phase advantageously comprises, besides the perlite particles, at least one additional filler, which is preferably lamellar, and at least one colouring agent, preferably chosen from pigments.

Preferably, the composition according to the invention is a foundation powder, in particular with a matt effect.

According to one particularly preferred embodiment, the said solid makeup and/or care cosmetic composition that is in the form of a powder comprises, limits inclusive and expressed as weight of solids for each of the compounds considered, relative to the total weight of the composition, at least:
- 50% to 90% of fillers, preferably lamellar fillers, including at least a content of perlite(s) in particle form of greater than or equal to 20%,
- 1% to 10% of non-volatile oil(s),
- 0 to 40% of colouring agent(s), preferably chosen from pigments,
- 0% of water.

According to a second aspect of the invention, a subject of the present invention is also a process for making up and/or caring for keratin materials, in particular the skin, preferably facial skin and especially the cheeks, the forehead, the temples, the chin and the nose, in which a composition as defined previously is applied to the said keratin materials.

Pulverulent Phase

A solid composition according to the invention advantageously has a content of pulverulent phase of greater than or equal to 35% by weight, in particular greater than or equal to 40% by weight, preferentially ranging from 50% to 99% by weight, better still from 60% to 98% by weight and even more preferentially from 75% to 96% by weight relative to the total weight of the composition.

According to the present invention, the pulverulent phase comprises at least one filler chosen from at least one perlite in particle form.

Fillers

The term "fillers" should be understood as meaning colourless or white solid particles of any form, which are in a form that is insoluble and dispersed in the medium of the composition. Mineral or organic in nature, they make it possible to confer softness, mattness and uniformity of makeup on the composition.

The fillers used in the compositions according to the present invention may be in lamellar (or platelet), spherical (or globular) form, in the form of fibres or in any other intermediate form between these defined forms. Preferably, the composition according to the present invention comprises predominantly, or even exclusively, lamellar fillers. The fillers may be present in a content ranging from 20% to 99% by weight, preferably from 50% to 98% by weight and more preferentially from 75% to 96% by weight relative to the total weight of the composition.

Perlite Particles

Perlite is generally obtained from natural glass of volcanic origin, of light-grey or glossy black colour, resulting from the rapid cooling of lava, and which is in the form of small particles resembling pearls. When heated above 800° C., perlite has the particular feature of losing the water it contains and of adopting a porous expanded form (representing from four to twenty times its initial volume), enabling it to absorb large amounts of liquid, in particular of oil and water. It then has a white colour.

Perlite, which is of mineral origin, is directly extracted from the ground and then finely ground to obtain a very fine white powder: perlite powder or perlite particles.

Perlite particles are thus particles of amorphous mineral materials, which are advantageously expanded, derived from at least one volcanic rock.

These particles comprise at least two elements chosen from silicon, aluminium and magnesium.

More particularly, these mineral materials are obtained by thermal expansion of a volcanic or "effusive" rock comprising from 1% to 10% by weight of water and preferably 1% to 5% by weight of water and less than 10% by weight of crystalline rock relative to the total weight of the rock composition and preferably followed by grinding. The temperature of the expansion process may range from 700 to 1500° C. and preferably from 800 to 1100° C. The expansion process described in U.S. Pat. No. 5,002,698 may especially be used.

Volcanic or "effusive" rocks are generally produced by the rapid cooling of liquid magma in contact with air or water (quenching phenomenon giving a hyaline rock). The volcanic rocks that may be used according to the present invention are chosen from those defined according to the Streckeisen classification (1974). Among these volcanic rocks, mention may be made especially of trachytes, latites, andesites, basalts, rhyolites and dacites. Rhyolites and dacites are particularly suitable for use, and even more particularly rhyolites.

The perlite particles that may be used according to the invention are preferably aluminosilicates of volcanic origin. They advantageously have the following composition:
70.0-75.0% by weight of silica $SiO_2$
12.0-15.0% by weight of oxide of aluminium oxide $Al_2O_3$
3.0-5.0% of sodium oxide $Na_2O$
3.0-5.0% of potassium oxide $K_2O$
0.5-2% of iron oxide $Fe_2O_3$→
0.2-0.7% of magnesium oxide $MgO$
0.5-1.5% of calcium oxide $CaO$
0.05-0.15% of titanium oxide $TiO_2$ In the implementation of the present invention, the perlite undergoes a first milling step so as to form perlite particles, and is dried and then calibrated. The product obtained, known as perlite ore, is grey-coloured and has a size of about 100 μm. The perlite ore is then expanded (1000° C./2 seconds) to give more or less white particles. When the temperature reaches 850-900° C., the water trapped in the structure of the material evaporates and brings about the expansion of the material relative to its original volume. The expanded perlite particles in accordance with the invention may be obtained via the expansion process described in U.S. Pat. No. 5,002,698.

Preferably, the perlite particles used are then milled in a second milling step in order further to reduce the size of the perlite particles used; in this case, they are referred to as expanded milled perlite (EMP). They preferably have a particle size defined by a median diameter $D_{50}$ ranging from 0.5 to 50 μm and preferably from 1 to 40 μm.

Preferentially, the perlite particles have a platelet shape; they are consequently usually called lamellar fillers, as opposed to spherical fillers, of globular shape.

The perlite particles advantageously have a coefficient of expansion of from 2 to 70.

Preferentially, the perlite particles have an untamped density at 25° C. ranging from 10 to 400 kg/m$^3$ (standard DIN 53468) and preferably from 10 to 300 kg/m$^3$.

According to one particular embodiment of the invention, the perlite particles have a silica content of greater than or equal to 65% by weight relative to the total weight of the composition of the material. According to one particular embodiment of the invention, the perlite particles have a spontaneous pH, measured at 25° C. in a dispersion in water at 10% by weight, ranging from 6 to 8.

Preferably, the expanded perlite particles according to the invention have a water-absorbing capacity, measured at the wet point, ranging from 200% to 1500% and preferably from 250% to 800%.

The wet point corresponds to the amount of water that needs to be added to 1 g of particle in order to obtain a homogeneous paste. This method is derived directly from that of the oil uptake applied to solvents. The measurements are taken in the same manner by means of the wet point and the flow point, which have, respectively, the following definitions:
wet point: weight expressed in grams per 100 g of product corresponding to the production of a homogeneous paste during the addition of a solvent to a powder;
flow point: weight expressed in grams per 100 g of product at and above which the amount of solvent is greater than the capacity of the powder to retain it. This is reflected by the production of a more or less homogeneous mixture that flows over the glass plate.
The wet point and the flow point are measured according to the following protocol:
Protocol for Measuring the Water Absorption
1) Equipment Used
Glass plate (25×25 mm)
Spatula (wooden shaft and metal part, 15×2.7 mm)
Silk-bristled brush
Balance
2) Procedure
The glass plate is placed on the balance and 1 g of perlite particles is weighed out. The beaker containing the solvent and the liquid sampling pipette is placed on the balance. The solvent is gradually added to the powder, the whole being regularly blended (every 3 to 4 drops) with the spatula.

The weight of solvent needed to obtain the wet point is noted. Further solvent is added and the weight which makes it possible to reach the flow point is noted. The average of three tests will be determined.

The perlite particles used according to the invention are especially commercially available from the company World minerals under the trade name Perlite P1430, Perlite P2550, Perlite P2040 or OpTiMat™ 1430 OR or 2550 OR.

The perlite particles are present in a composition in accordance with the present invention in a content of greater than or equal to 20% by weight relative to the total weight of the composition, preferably in a content strictly greater than 20% by weight relative to the total weight of the composition, for example ranging from 22% to 80% by weight relative to the total weight of the composition, better still from 25% to 70% by weight relative to the total weight of the composition, preferentially from 28% to 60% by weight relative to the total weight of the composition and even more preferentially from 30% to 50% by weight relative to the total weight of the composition.

The perlite particles and the pulverulent phase may be present in the composition in a respective total content such that the weight ratio of the perlite particles to the pulverulent phase ranges from 0.2 to 1, better still from 0.22 to 0.95, even better still from 0.25 to 0.9, preferably from 0.30 to 0.75 and more preferentially from 0.4 to 0.6.

The pulverulent phase according to the present invention preferably comprises at least one additional filler, i.e. besides the perlite particles, the composition preferably comprises at least one filler other than the perlite particles.

Additional Filler(s)

The additional fillers advantageously used in a composition according to the invention may be in lamellar (or platelet) or spherical (or globular) form, in the form of fibres or in any other intermediate form between these defined forms.

Preferably, the composition according to the present invention comprises predominantly, or even exclusively, lamellar fillers.

These fillers according to the invention may or may not be surface-coated, and in particular they may be surface-treated with silicones, amino acids, fluoro derivatives or any other substance that promotes the dispersion and compatibility of the filler in the composition.

Preferably, a composition according to the invention comprises at least one additional mineral filler. Preferably, this (these) mineral filler(s) are chosen from talc, mica, silica, magnesium aluminium silicate, trimethyl siloxysilicate, kaolin, bentone, calcium carbonate, magnesium hydrogen carbonate, hydroxyapatite, boron nitride, hollow silica microspheres (Silica Beads from Maprecos), glass or ceramic microcapsules, silica-based fillers, for instance Aerosil 200 or Aerosil 300; Sunsphere H-33 and Sunsphere H-51 sold by Asahi Glass; Chemicelen sold by Asahi Chemical; composites of silica and of titanium dioxide, for instance the TSG series sold by Nippon Sheet Glass, and fluorphlogopite, and mixtures thereof.

Preferably, a composition according to the invention comprises at least one additional organic filler. Preferably, this (these) mineral/organic filler(s) are chosen from polyamide powders (Nylon® Orgasol from Atochem), poly-β-alanine powders and polyethylene powders, polytetrafluoroethylene powders (Teflon), lauroyllysine, starch, tetrafluoroethylene polymer powders, hollow polymer microspheres, for example comprising an (alkyl)acrylate, such as Expancel® (Nobel Industrie), metal soaps derived from organic carboxylic acids containing from 8 to 22 carbon atoms and preferably from 12 to 18 carbon atoms, for example zinc stearate, magnesium stearate, lithium stearate, zinc laurate, magnesium myristate, Polypore® L200 (Chemdal Corporation), silicone resin microbeads (for example Tospearl® from Toshiba), polyurethane powders, in particular powders of crosslinked polyurethane comprising a copolymer, the said copolymer comprising trimethylol hexyl lactone, for instance the hexamethylene diisocyanate/trimethylol hexyl lactone polymer sold under the name Plastic Powder D-400® or Plastic Powder D-800® by the company Toshiki, carnauba microwaxes, such as the product sold under the name Micro Care 350® by the company Micro Powders, synthetic microwaxes, such as the product sold under the name MicroEase 114S® by the company Micro Powders, microwaxes formed from a mixture of carnauba wax and polyethylene wax, such as those sold under the names Micro Care 300® and 310® by the company Micro Powders, microwaxes formed from a mixture of carnauba wax and of synthetic wax, such as the product sold under the name Micro Care 325® by the company Micro Powders, polyethylene microwaxes, such as those sold under the names Micropoly 200®, 220®, 220L® and 250S® by the company Micro Powders; fibres of synthetic or natural, mineral or organic origin. They may be short or long, individual or organized, for example braided, and hollow or solid. They may have any shape and may especially have a circular or polygonal (square, hexagonal or octagonal) cross section depending on the specific application envisaged. In particular, their ends are blunted and/or polished to prevent injury. The fibres have a length ranging from 1 μm to 10 mm, preferably from 0.1 mm to 5 mm and better still from 0.3 mm to 3 mm. Their cross section may be included in a circle with a diameter ranging from 2 nm to 500 μm, preferably ranging from 100 nm to 100 μm and better still from 1 μm to 50 μm. As fibres that can be used in the compositions according to the invention, mention may be made of non-rigid fibres such as polyamide (Nylon®) fibres or rigid fibres such as polyimideamide fibres, for instance those sold under the names Kermel® and Kermel Tech® by the company Rhodia or poly(p-phenyleneterephthalamide) (or aramid) fibres sold especially under the name Kevlar® by the company DuPont de Nemours, and mixtures thereof.

As representatives of such fillers preferably used in the context of the present invention, mention may be made especially of talc, mica, starch, fluorphlogopite, clays such as magnesium aluminium silicate, or hollow polymer microspheres.

The additional fillers may be present in the composition in a content of greater than or equal to 20% by weight relative to the weight of the composition, for example ranging from 1% to 79% by weight, preferably from 10% to 60% by weight and even more preferentially from 20% to 50% by weight, relative to the total weight of the composition.

The perlite particles and the additional filler(s) may be present in the composition in a respective total content such that the weight ratio of the perlite particles to the additional filler(s) may range from 0.2 to 3, preferably from 0.25 to 1 and more preferentially from 0.3 to 0.8.

The pulverulent phase also preferably comprises colouring agents.

Colouring Agent(s)

The colouring agent(s) or dyestuff(s) according to the invention are preferably chosen from pigments, nacres and reflective particles, and mixtures thereof. Preferably, a composition according to the invention comprises at least one pigment.

Pigments

The term "pigments" should be understood as meaning white or coloured, mineral or organic particles of any shape, which are insoluble in the physiological medium, and which are intended to colour the composition.

The pigments may be white or coloured, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

The organic pigments may be chosen from the materials below, and mixtures thereof:
cochineal carmine,
organic pigments of azo dyes, anthraquinone dyes, indigoid dyes, xanthene dyes, pyrene dyes, quinoline dyes, triphenylmethane dyes and fluoran dyes.

Among the organic pigments, mention may be made especially of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic dyestuffs mentioned previously are mentioned in the publication "International Cosmetic Ingredient Dictionary and Handbook", 1997 edition, pages 371 to 386 and 524 to 528, published by The Cosmetic, Toiletries and Fragrance Association, the content of which is incorporated into the present patent application by reference.

A composition according to the invention may comprise a content of pigments ranging from 0 to 30% by weight relative to the total weight of the composition, preferably ranging from 2% to 20% by weight and preferentially ranging from 4% to 10% by weight, relative to the total weight of the composition.

Nacres

The terms "nacres" should be understood as meaning coloured particles of any form, which may or may not be iridescent, especially produced by certain mollusks in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, and nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery colour or glint.

As illustrations of nacres that may be introduced into the composition, mention may be made of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles having a glass substrate coated with titanium oxide are especially sold under the name Metashine MC1080RY by the company Toyal.

Finally, examples of nacres that may also be mentioned include polyethylene terephthalate flakes, especially those sold by the company Meadowbrook Inventions under the name Silver 1P 0.004X0.004 (silver flakes).

The compositions according to the invention may have a nacre content ranging from 0 to 30% by weight, for example from 0.01% to 5% by weight relative to the total weight of the composition.

Reflective Particles

The term "reflective particles" denotes particles whose size, structure, especially the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle.

The reflective particles may be selected so as not to significantly alter the colouration effect generated by the colouring agents with which they are combined, and more particularly so as to optimize this effect in terms of colour yield. They may more particularly have a yellow, pink, red, bronze, orange, brown, gold and/or coppery colour or tint.

These particles may have varied forms and may especially be in platelet or globular form, in particular in spherical form.

The reflective particles, whatever their form, may or may not have a multilayer structure and, in the case of a multilayer structure, may have, for example, at least one layer of uniform thickness, in particular of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or inorganic materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company.

Use may also be made of particles comprising a metallic substrate such as silver, aluminium, iron, chromium, nickel, molybdenum, gold, copper, zinc, tin, manganese, steel, bronze or titanium, said substrate being coated with at least one layer of at least one metal oxide such as titanium oxide, aluminium oxide, iron oxide, cerium oxide, chromium oxide or silicon oxides, and mixtures thereof.

Examples that may be mentioned include aluminium powder, bronze powder or copper powder coated with $SiO_2$ sold under the name Visionaire by the company Eckart.

The compositions according to the invention may have a content of reflective particles ranging from 0 to 30% by weight, for example from 0.01% to 5% by weight, relative to the total weight of the composition.

Preferably, the pulverulent phase comprises, besides perlite particles, at least one compound chosen from:

additional mineral fillers, advantageously chosen from talc and mica, and a mixture thereof, organic pigments advantageously chosen from the pigments certified D&C by the Food & Drug Administration as listed in the section "Color Additives—Batch Certified by the U.S. Food and Drug Administration" of the CTFA; mention may be made especially of Blue 1 and 4, Brown 1, Ext. Violet 2, Ext. Yellow 7, Green 3, 5, 6 and 8, Orange 4, 5, 10 and 11, Red 4, 6, 7, 17, 21, 22, 27, 28, 30, 36 and 40, Violet 2, Yellow 5, 6, 7, 8, 10 and 11, and mixtures thereof, mineral pigments advantageously chosen from iron oxide, titanium oxide, zirconium oxide, cerium oxide, zinc oxide or chromium oxide, ferric blue, manganese violet, ultramarine blue, pink or violet, chromium hydrate, chromium hydroxide and bismuth oxychloride, and mixtures thereof.

Liquid Fatty Phase

A solid cosmetic composition according to the invention comprises at least one liquid fatty phase.

This fatty phase may advantageously serve as binder for the said pulverulent phase.

A liquid fatty phase preferably comprises at least one non-volatile oil.

The term "liquid" refers to a composition that is liquid at room temperature (25° C.) and atmospheric pressure (760 mmHg).

The term "oil" means a water-immiscible non-aqueous compound that is liquid at room temperature (25° C.) and at atmospheric pressure (760 mmHg).

The term "non-volatile oil" means an oil that remains on the skin or the keratin fibre at room temperature and pressure. More precisely, a non-volatile oil has an evaporation rate strictly less than 0.01 mg/cm$^2$/min.

A solid composition according to the invention advantageously has a content of liquid fatty phase, and in particular of non-volatile oil(s), of less than or equal to 15% by weight, in particular less than or equal to 10% by weight, more particularly 8% by weight and especially ranging from 1% to 6% by weight relative to the total weight of the composition.

A solid composition according to the invention preferably comprises at least one non-volatile oil chosen from non-volatile hydrocarbon-based and silicone oils, and mixtures thereof.

According to one particular embodiment, the said composition comprises at least one hydrocarbon-based oil, preferably of synthetic esters type, and at least one silicone oil, preferably of the phenyl trimethicone type such as DC556.

Hydrocarbon-Based Non-Volatile Oil

A composition according to the invention may also comprise one or more non-volatile hydrocarbon-based oils.

Additional non-volatile hydrocarbon-based oils that may especially be mentioned include:

hydrocarbon-based oils of plant origin, such as phytostearyl esters, such as phytostearyl oleate, phytostearyl isostearate and lauroyl/octyldodecyl/phytostearyl glutamate; triglycerides formed from fatty acid esters of glycerol, in particular whose fatty acids may have chain lengths ranging from $C_{18}$ to $C_{36}$, these oils possibly being linear or branched, and saturated or unsaturated; these oils may especially be heptanoic or octanoic triglycerides, shea oil, alfalfa oil, poppy oil, pumpkin oil, millet oil, barley oil, quinoa oil, rye oil, candlenut oil, passionflower oil, shea butter oil, aloe oil, sweet almond oil, peach stone oil, groundnut oil, argan oil, avocado oil, baobab oil, borage oil, broccoli oil, calendula oil, camellina oil, carrot oil, safflower oil, hemp oil, rapeseed oil, cottonseed oil, coconut oil, marrow seed oil, wheatgerm oil, jojoba oil, lily oil, macadamia oil, corn oil, meadowfoam oil, St-John's wort oil, monoi oil, hazelnut oil, apricot kernel oil, walnut oil, olive oil, evening primrose oil, palm oil, blackcurrant pip oil, kiwi seed oil, grape seed oil, pistachio oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company Stéarineries Dubois or those sold under the names Miglyol 810®, 812® and 818® by the company Dynamit Nobel;

synthetic ethers containing from 10 to 40 carbon atoms;

synthetic esters, for instance the oils of formula $R_1COOR_2$, in which $R_1$ represents at least one linear or branched fatty acid residue containing from 1 to 40 carbon atoms and $R_2$ represents a hydrocarbon-based chain, which is especially branched, containing from 1 to 40 carbon atoms, on condition that $R_1+R_2 \geq 10$. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotridecyl isononanoate, octyl isononanoate, hydroxylated esters, for instance isostearyl lactate and diisostearyl malate;

polyol esters and pentaerythritol esters, for instance dipentaerythrityl tetrahydroxystearate/tetraisostearate;

esters of diol dimers and of diacid dimers;

copolymers of diol dimer and of diacid dimer and esters thereof, such as dilinoleyl diol dimer/dilinoleic dimer copolymers, and esters thereof;

copolymers of polyols and of diacid dimers, and esters thereof;

fatty alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol;

$C_{12}$-$C_{22}$ higher fatty acids, such as oleic acid, linoleic acid and linolenic acid, and mixtures thereof;

dialkyl carbonates, the two alkyl chains possibly being identical or different, such as dicaprylyl carbonate;

oils with a molar mass of between about 400 and about 10 000 g/mol, in particular about 650 to about 10 000 g/mol, in particular from about 750 to about 7500 g/mol and more particularly ranging from about 1000 to about 5000 g/mol; mention may be made especially, alone or as a mixture, of (i) lipophilic polymers such as polybutylenes, polyisobutylenes, for example hydrogenated, polydecenes and hydrogenated polydecenes, vinylpyrrolidone copolymers, such as the vinylpyrrolidone/1-hexadecene copolymer, and polyvinylpyrrolidone (PVP) copolymers, such as the copolymers of a $C_2$-$C_{30}$ alkene, such as $C_3$-$C_{22}$, and combinations thereof; (ii) linear fatty acid esters containing a total carbon number ranging from 35 to 70, for instance pentaerythrityl tetrapelargonate; (iii) hydroxylated esters such as polyglyceryl-2 triisostearate; (iv) aromatic esters such as tridecyl trimellitate; (v) esters of fatty alcohols or of branched $C_{24}$-$C_{28}$ fatty acids, such as those described in U.S. Pat. No. 6,491,927 and pentaerythritol esters, and especially triisoarachidyl citrate, pentaerythrityl tetraisononanoate, glyceryl triisostearate, glyceryl 2-tridecyltetradecanoate, pentaerythrityl tetraisostearate, poly(2-glyceryl)tetraisostearate or pentaerythrityl 2-tetradecyltetradecanoate; (vi) diol dimer esters and polyesters, such as esters of diol dimer and of fatty acid, and esters of diol dimer and of diacid.

According to one particular embodiment, a composition according to the invention is free of additional non-volatile hydrocarbon-based oil(s).

Non-Volatile Silicone Oils

According to one preferred embodiment of the invention, the compositions according to the invention comprise at least one non-volatile silicone oil.

Preferentially, a composition according to the invention comprises at least one volatile hydrocarbon-based oil, advantageously chosen from $C_{12}$-$C_{15}$ alkyl benzoates, as a mixture with one or more non-volatile silicone oil(s).

The non-volatile silicone oil that may be used in the invention may be chosen from silicone oils with a viscosity at 25° C. of greater than or equal to 9 centistokes (cSt) ($9 \times 10^{-6}$ m$^2$/s) and less than 800 000 cSt, preferably between 50 and 600 000 cSt and preferably between 100 and 500 000 cSt. The viscosity of this silicone may be measured according to standard ASTM D-445.

Among these silicone oils, two types of oil may be distinguished, according to whether or not they contain phenyl.

Representative examples of these non-volatile linear silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

Thus, non-phenyl non-volatile silicone oils that may be mentioned include:
PDMSs comprising alkyl or alkoxy groups, which are pendent and/or at the end of the silicone chain, these groups each containing from 2 to 24 carbon atoms,
PDMSs comprising aliphatic groups, or functional groups such as hydroxyl, thiol and/or amine groups,
polyalkylmethylsiloxanes optionally substituted with a fluorinated group, such as polymethyltrifluoropropyldimethylsiloxanes,
polyalkylmethylsiloxanes substituted with functional groups such as hydroxyl, thiol and/or amine groups,
polysiloxanes modified with fatty acids, fatty alcohols or polyoxyalkylenes, and mixtures thereof.

According to one particular embodiment, a composition according to the invention contains at least one non-phenyl linear silicone oil.

The non-phenyl linear silicone oil may be chosen especially from the silicones of formula:

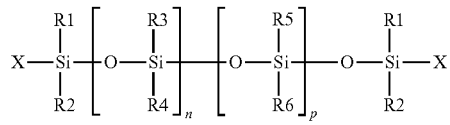

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound.

As non-volatile silicone oils that may be used according to the invention, mention may be made of those for which:
the substituents $R_1$ to $R_6$ and X represent a methyl group, and p and n are such that the viscosity is 500 000 cSt,
such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker, the substituents $R_1$ to $R_6$ and X represent a methyl group, and p and n are such that the viscosity is 350 cSt, such as the product sold under the name Dow Corning 200 Fluid 350 CS by the company Dow Corning, the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to one preferred embodiment variant, a composition according to the invention contains at least one phenyl silicone oil.

Representative examples of these non-volatile phenyl silicone oils that may be mentioned include:
the phenyl silicone oils corresponding to the following formula:

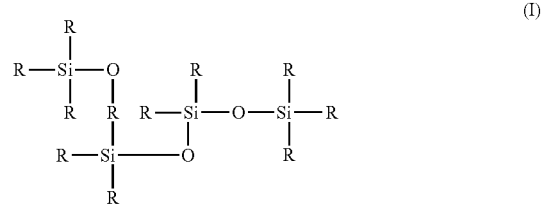

in which formula (I) the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.

the phenyl silicone oils corresponding to the following formula:

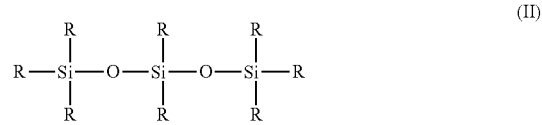

in which formula (II) the groups R represent, independently of each other, a methyl or a phenyl, with the proviso that at least one group R represents a phenyl. Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes.

the phenyl silicone oils corresponding to the following formula:

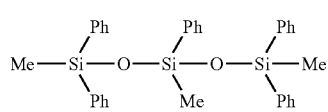
(III)

in which formula (III) Me represents methyl, Ph represents phenyl. Such a phenyl silicone is especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane). The reference Dow Corning 554 Cosmetic Fluid may also be used.

the phenyl silicone oils corresponding to the following formula:

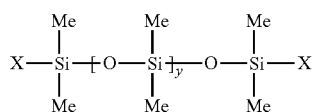
(IV)

in which formula (IV) Me represents methyl, y is between 1 and 1000 and X represents —$CH_2$—$CH(CH_3)$(Ph).

the phenyl silicone oils corresponding to formula (V) below:

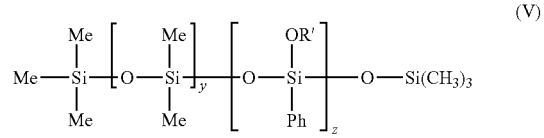
(V)

in which formula (V) Me is methyl and Ph is phenyl, OR represents a group —$OSiMe_3$ and y is 0 or ranges between 1 and 1000, and z ranges between 1 and 1000, such that compound (V) is a non-volatile oil.

According to a first embodiment, y ranges between 1 and 1000. Use may be made, for example, of trimethyl siloxyphenyl dimethicone, sold especially under the reference Belsil PDM 1000 sold by the company Wacker.

According to a second embodiment, y is equal to 0. Use may be made, for example, of phenyl trimethylsiloxy trisiloxane, sold especially under the reference Dow Corning 556 Cosmetic Grade Fluid, the phenyl silicone oils corresponding to formula (VI) below, and mixtures thereof:

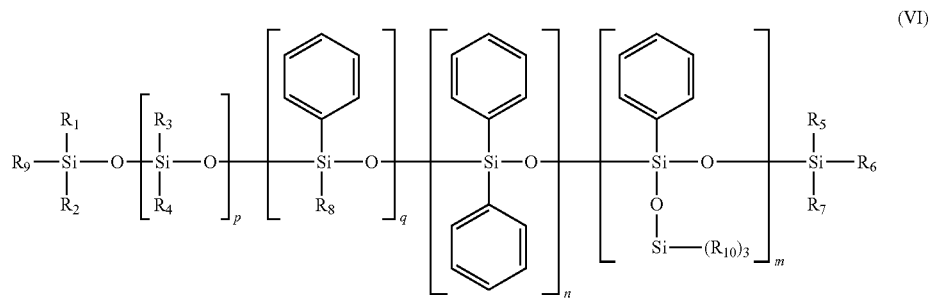
(VI)

in which formula (VI):
$R_1$ to $R_{10}$, independently of each other, are saturated or unsaturated, linear, cyclic or branched $C_1$-$C_{30}$ hydrocarbon-based radicals,
m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

the phenyl silicone oils corresponding to formula (VII) below, and mixtures thereof:

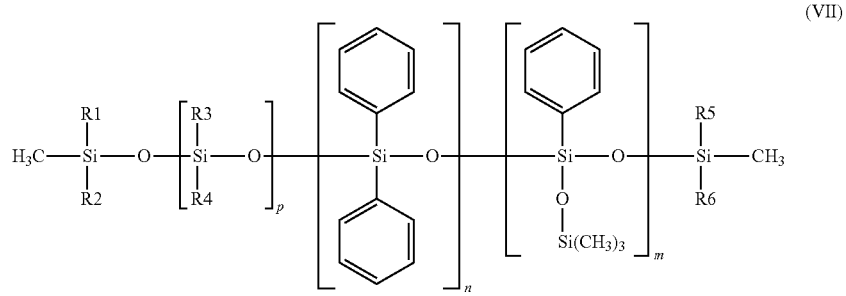
(VII)

in which formula (VII):

R$_1$ to R$_6$, independently of each other, are saturated or unsaturated, linear, cyclic or branched C$_1$-C$_{30}$ hydrocarbon-based radicals, m, n and p are, independently of each other, integers between 0 and 100, with the proviso that the sum n+m is between 1 and 100.

Preferably, R$_1$ to R$_6$, independently of each other, represent a saturated, linear or branched C$_1$-C$_{30}$ and especially C$_1$-C$_{12}$ hydrocarbon-based radical and in particular a methyl, ethyl, propyl or butyl radical.

R$_1$ to R$_6$ may especially be identical, and in addition may be a methyl radical.

Preferably, m=1 or 2 or 3, and/or n=0 and/or p=0 or 1 may apply, in formula (VII).

the phenyl silicone oils corresponding to formula (VIII), and mixtures thereof:

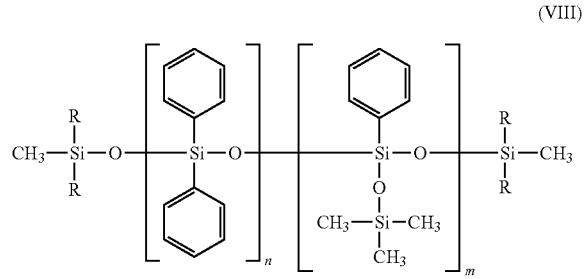

(VIII)

in which formula (VIII):

R is a C$_1$-C$_{30}$ alkyl radical, an aryl radical or an aralkyl radical, n is an integer ranging from 0 to 100, and m is an integer ranging from 0 to 100, with the proviso that the sum n+m ranges from 1 to 100.

In particular, the radicals R of formula (VIII) and R$_1$ to R$_{10}$ defined previously may each represent a linear or branched, saturated or unsaturated alkyl radical, especially of C$_2$-C$_{20}$, in particular C$_3$-C$_{16}$ and more particularly C$_4$-C$_{10}$, or a monocyclic or polycyclic C$_6$-C$_{14}$ and especially C$_{10}$-C$_{13}$ aryl radical, or an aralkyl radical whose aryl and alkyl residues are as defined previously.

Preferably, R of formula (VIII) and R$_1$ to R$_{10}$ may each represent a methyl, ethyl, propyl, isopropyl, decyl, dodecyl or octadecyl radical, or alternatively a phenyl, tolyl, benzyl or phenethyl radical.

According to one embodiment, a phenyl silicone oil of formula (VIII) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt) may be used.

As phenyl silicone oils of formula (VIII), it is especially possible to use phenyl trimethicones such as DC556 from Dow Corning (22.5 cSt), the oil Silbione 70663V30 from Rhône-Poulenc (28 cSt) or diphenyl dimethicones such as Belsil oils, especially Belsil PDM1000 (1000 cSt), Belsil PDM 200 (200 cSt) and Belsil PDM 20 (20 cSt) from Wacker. The values in parentheses represent the viscosities at 25° C.

the phenyl silicone oils corresponding to the following formula, and mixtures thereof:

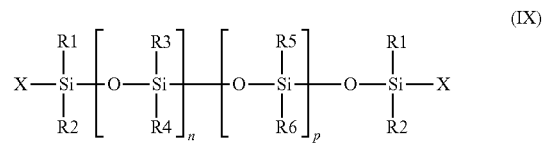

(IX)

in which formula (IX):

R$_1$, R$_2$, R$_5$ and R$_6$ are, together or separately, an alkyl radical containing 1 to 6 carbon atoms, R$_3$ and R$_4$ are, together or separately, an alkyl radical containing from 1 to 6 carbon atoms or an aryl radical, X is an alkyl radical containing from 1 to 6 carbon atoms, a hydroxyl radical or a vinyl radical, n and p being chosen so as to give the oil a weight-average molecular mass of less than 200 000 g/mol, preferably less than 150 000 g/mol and more preferably less than 100 000 g/mol.

The phenyl silicones that are most particularly suitable for use in the invention are those corresponding to formulae (II) and especially to formulae (III), (V) and (VIII) hereinabove.

More particularly, the phenyl silicones are chosen from phenyl trimethicones, phenyl dimethicones, phenyl-trimethylsiloxydiphenylsiloxanes, diphenyl dimethicones, diphenylmethyldiphenyltrisiloxanes and 2-phenylethyl trimethylsiloxysilicates, and mixtures thereof.

Preferably, the weight-average molecular weight of the non-volatile phenyl silicone oil according to the invention ranges from 500 to 10 000 g/mol.

It should be noted that, among the silicone compounds according to the invention, phenyl silicone oils prove to be particularly advantageous.

Volatile Oil

The liquid fatty phase may optionally comprise at least one volatile oil.

The term "volatile oil" means an oil (or non-aqueous medium) that can evaporate on contact with the skin in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits included.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing the said oil or the said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

This volatile oil may be a hydrocarbon-based oil, silicone oil or fluoro oil. It is preferably a hydrocarbon-based oil.

The term "hydrocarbon-based oil" means an oil mainly containing hydrogen and carbon atoms.

The term "silicone oil" means an oil containing at least one silicon atom, and especially containing Si—O groups. According to one embodiment, the said composition comprises less than 10% by weight of non-volatile silicone oil(s), relative to the total weight of the composition, better still less than 5% by weight, or even is free of silicone oil.

The term "fluoro oil" means an oil comprising at least one fluorine atom.

The oils may optionally comprise oxygen, nitrogen, sulfur and/or phosphorus atoms, for example in the form of hydroxyl or acid radicals.

The volatile oils may be chosen from hydrocarbon-based oils containing from 8 to 16 carbon atoms, and especially $C_8$-$C_{16}$ branched alkanes (also known as isoparaffins), for instance isododecane, isodecane and isohexadecane.

The volatile hydrocarbon-based oil may also be a linear volatile alkane containing 7 to 17 carbon atoms, in particular 9 to 15 carbon atoms and more particularly 11 to 13 carbon atoms. Mention may be made especially of n-nonadecane, n-decane, n-undecane, n-dodecane, n-tridecane, n-tetradecane, n-pentadecane and n-hexadecane, and mixtures thereof.

Preferably, the composition is free of volatile oil. Such an absence of volatile oil makes it possible, where appropriate, to dispense with a perfectly leaktight conditioning assembly for the said composition.

Aqueous Phase

The composition according to the invention may comprise an aqueous phase.

This aqueous phase, when present, is used in an amount that is compatible with the pulverulent galenical form required according to the invention.

The aqueous phase may be a demineralized water or alternatively a floral water such as cornflower water and/or a mineral water such as Vittel water, Lucas water or La Roche Posay water and/or a spring water.

The aqueous phase may also comprise a polyol that is miscible with water at room temperature (25° C.) chosen especially from polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers; and mixtures thereof.

The composition according to the invention may comprise a polyol that is miscible with water at room temperature. Such polyols may promote the moisturization of the surface of the skin on which the composition is applied.

In addition, the composition according to the invention may comprise a monoalcohol containing from 2 to 6 carbon atoms, such as ethanol or isopropanol.

A composition according to the invention advantageously comprises less than 5% by weight of aqueous phase, and in particular of water, relative to the total weight of the composition. Preferentially, a composition according to the invention is free of aqueous phase, and in particular free of water.

Adjuvants

The composition may comprise other ingredients (adjuvants) usually used in cosmetics, such as preserving agents, cosmetic active agents, moisturizers, UV-screening agents, thickeners and fragrances.

Needless to say, a person skilled in the art will take care to select the optional adjuvant(s) added to the composition according to the invention such that the advantageous properties intrinsically associated with the composition in accordance with the invention are not, or are not substantially, adversely affected by the envisaged addition.

Assembly

According to another aspect, the invention also relates to a cosmetic assembly comprising:

i) a container delimiting one or more compartment(s), the said container being closed by a closing member and optionally not being leaktight; and ii) a makeup and/or care composition in accordance with the invention placed inside the said compartment(s).

The container may be, for example, in the form of a jar or a box.

The closing member may be in the form of a lid comprising a cap mounted so as to be able to move by translation or by pivoting relative to the container housing the said makeup and/or care composition(s).

EXAMPLE

A solid cosmetic composition, in the form of a compact powder, in particular a pressed powder, of a foundation powder according to the invention was prepared as followed and then tested according to various cosmetic evaluation criteria.

| Phases | Compounds | % content |
|---|---|---|
| 1 | Mineral pigments of metal oxide type | 6 |
|  | Perlite (Optimat 2550 OR from World Minerals) | 43 |
|  | Talc | 43 |
|  | Magnesium stearate | 3 |
| 2 | Glyceryl triisostearate | 2 |
|  | Phenyl trimethicone (DC556 from Dow Corning) | 2 |
| 3 | Caprylyl glycol (Dermosoft Octiol ® from Dr. Straetmans) | 1 |

The procedure below was used to prepare the compositions according to the invention.

The compounds of phase 1 are weighed out and then dispersed in a Novamix 1 L mixer-disperser for 3 minutes 30 seconds with paddle stirring at 3000 rpm and decaking at 2700 rpm. The compounds of phases 2 and 3 are then weighed out and added to phase 1 in order to be mixed together for 5 minutes by paddle stirring at 3000 rpm.

Evaluation of the Composition:

An evaluation protocol was implemented on a panel of 16 experienced people, and the result concerning the softness of touch, the application (amount taken up, ease of application, adherence on application), the texture, the makeup result (uniformity, powdery effect, coverage, colour effect, matting effect associated with the absorption of bodily fluids such as water, sweat and/or sebum), the comfort throughout the day, the remanence over time, the remanence of the matt effect over time and the ease of removal of a composition according to the invention was evaluated by these same people.

Results

The panel said that it was satisfied regarding these criteria, the makeup result (in particular the matting effect with good control of fluid secretions such as water, oil and sweat, the coverage, the natural effect), the comfort on application, the sensation on use, the remanence over time, the remanence of the matt effect over time and the ease of removal being the most satisfactory criteria.

It is understood that, in the context of the present invention, the weight percentages given for a compound or a family of compounds are always expressed as weight of solids of the compound in question.

Throughout the application, the term "comprises one" or "includes one" should be understood as meaning "comprising at least one" or "including at least one", unless otherwise specified.

The invention claimed is:

1. A solid cosmetic composition, comprising:
a pulverulent phase in an amount of greater than or equal to 35% by weight relative to a total weight of the composition consisting of (1) perlite particles in a content of greater than or equal to 20% by weight relative to the total weight of the composition, (2) at least one lamellar filler, (3) optionally at least one coloring agent, and (4) optionally at least one additional filler selected from the group consisting of talc, mica, silica, magnesium aluminium silicate, kaolin, bentone, calcium carbonate, magnesium hydrogen carbonate, hydroxyapatite, boron nitride, hollow silica microspheres, glass microcapsules, ceramic microcapsules, composites of silica and of titanium dioxide, fluorphlogopite, polyamide powders, poly-β-alanine powders, polyethylene powders, polytetrafluoroethylene powders, lauroyllysine, starch, tetrafluoroethylene polymer powders, hollow polymer microspheres comprising an (alkyl)acrylate, metal soaps derived from organic carboxylic acids containing from 8 to 22 carbon atoms, silicone resin microbeads, polyurethane powders, carnauba microwaxes, synthetic microwaxes, microwaxes formed from a mixture of carnauba wax and polyethylene wax, microwaxes formed from a mixture of carnauba wax and of synthetic wax, polyethylene microwaxes, fibres of synthetic origin, fibers of natural origin, fibers of mineral origin, fibers of organic origin, and mixtures thereof, and
a liquid fatty phase,
wherein
the composition is in a form of a powder, and
a weight ratio of the perlite particles to the liquid fatty phase ranges from 2 to 25.

2. The composition according to claim 1, wherein the pulverulent phase is present in an amount of greater than or equal to 50% by weight relative to the total weight of the composition.

3. The composition according to claim 1, wherein the pulverulent phase comprises at least one coloring agent selected from the group consisting of a nacre, a pigment and a reflective particle.

4. The composition according to claim 3, wherein a content of the coloring agent is greater than or equal to 0.01% by weight relative to the total weight of the composition.

5. The composition according to claim 1, wherein the liquid fatty phase is present in a content of less than or equal to 15% by weight relative to the total weight of the composition.

6. The composition according to claim 1, wherein the liquid fatty phase comprises a non-volatile oil.

7. The composition according to claim 6, wherein the non-volatile oil is selected from the group consisting of a non-volatile hydrocarbon-based oil, a silicone oil, and any mixture thereof.

8. The composition according to claim 1, wherein the at least one additional filler is present in a content of greater than or equal to 20% by weight relative to the total weight of the composition.

9. The composition according to claim 1, wherein a weight ratio of the perlite particles to the at least one additional filler ranges from 0.2 to 3.

10. The composition according to claim 1, wherein a weight ratio of the perlite particles to the pulverulent phase ranges from 0.2 to 1.

11. The composition according to claim 1, wherein the composition is a foundation powder.

12. A process for coating a face, the process comprising: applying the composition according claim 1 to the face.

13. The composition according to claim 1, which is in a form of a compacted powder.

14. The composition according to claim 1, wherein the pulverulent phase is present in an amount of greater than or equal to 50% by weight relative to the total weight of the composition and comprises at least one coloring agent selected from the group consisting of a nacre, a pigment and a reflective particle in an amount of greater than or equal to 0.01% by weight relative to the total weight of the composition, wherein the liquid fatty phase is present in a content of less than or equal to 15% by weight relative to the total weight of the composition, and wherein a weight ratio of the perlite particles to the at least one additional filler ranges from 0.2 to 3.

15. The composition according to claim 1, wherein the pulverulent phase includes at least one coloring agent selected from the group consisting of pigments, nacres, reflective particles, and mixtures thereof.

16. The composition according to claim 15, wherein the pulverulent phase includes at least one pigment.

17. The composition according to claim 1, wherein the pulverulent phase includes at least one additional filler selected from the group consisting of talc, mica, and mixtures thereof.

* * * * *